US009737650B2

(12) United States Patent
Coulthard et al.

(10) Patent No.: US 9,737,650 B2
(45) Date of Patent: *Aug. 22, 2017

(54) FLUID POUCH, SYSTEM, AND METHOD FOR STORING FLUID FROM A TISSUE SITE

(71) Applicant: KCI Licensing, Inc., San Antonio, TX (US)

(72) Inventors: Richard Daniel John Coulthard, Verwood (GB); Timothy Mark Robinson, Basingstoke (GB); Christopher Brian Locke, Bournemouth (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 599 days.

This patent is subject to a terminal disclaimer.

(21) Appl. No.: 14/229,457

(22) Filed: Mar. 28, 2014

(65) Prior Publication Data
US 2014/0343516 A1 Nov. 20, 2014

Related U.S. Application Data

(63) Continuation of application No. 12/617,792, filed on Nov. 13, 2009, now Pat. No. 8,728,044.
(Continued)

(51) Int. Cl.
*A61M 27/00* (2006.01)
*A61M 1/00* (2006.01)
*A61F 13/02* (2006.01)

(52) U.S. Cl.
CPC ....... *A61M 1/0088* (2013.01); *A61F 13/0203* (2013.01); *A61M 1/0001* (2013.01);
(Continued)

(58) Field of Classification Search
CPC .............. A61F 13/00029; A61F 13/022; A61F 13/0203–13/0226; A61M 1/0088–1/0098
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96.

(Continued)

*Primary Examiner* — Susan Su

(57) ABSTRACT

The illustrative embodiments described herein are directed to an apparatus, system, and method for storing liquid from a tissue site. The apparatus may include a drape having an aperture, and a fluid pouch coupled to the drape such that the fluid pouch is in fluid communication with the aperture. In one embodiment, the fluid pouch is operable to transfer reduced pressure to the aperture such that the liquid from the tissue site is drawn into the fluid pouch. The fluid pouch may have a cavity that stores the liquid that is drawn from the tissue site. In another embodiment, the fluid pouch may include at least one baffle. The fluid pouch may also include a fluid channel at least partially defined by the at least one baffle. The fluid channel may be operable to store liquid
(Continued)

from the tissue site when reduced pressure is applied through the fluid channel.

12 Claims, 7 Drawing Sheets

Related U.S. Application Data

(60) Provisional application No. 61/114,827, filed on Nov. 14, 2008.

(52) U.S. Cl.
CPC ... *A61M 1/0096* (2014.02); *A61M 2205/3331* (2013.01); *A61M 2205/3368* (2013.01); *A61M 2205/3389* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 3,867,939 A | 2/1975 | Moore et al. | |
| 4,080,970 A | 3/1978 | Miller | |
| 4,096,853 A | 6/1978 | Weigand | |
| 4,139,004 A | 2/1979 | Gonzalez, Jr. | |
| 4,149,541 A * | 4/1979 | Gammons | A61F 7/02 |
| | | | 5/421 |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A * | 8/1995 | Todd | A61M 1/0088 |
| | | | 15/420 |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,108,683 B2 * | 9/2006 | Zamierowski | A61M 1/0058 |
| | | | 604/304 |
| 7,520,872 B2 * | 4/2009 | Biggie | A61M 1/0088 |
| | | | 601/6 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0128578 A1 * | 9/2002 | Johnston | A47L 9/02 |
| | | | 602/43 |
| 2002/0143286 A1 | 10/2002 | Tumey | |
| 2004/0076662 A1 * | 4/2004 | Riesinger | A61F 13/00055 |
| | | | 424/445 |
| 2005/0137539 A1 | 6/2005 | Biggie et al. | |
| 2006/0079852 A1 | 4/2006 | Bubb et al. | |
| 2007/0055209 A1 | 3/2007 | Patel et al. | |
| 2008/0082059 A1 | 4/2008 | Fink et al. | |
| 2008/0195017 A1 * | 8/2008 | Robinson | A61F 13/00068 |
| | | | 602/44 |
| 2009/0082740 A1 * | 3/2009 | Lockwood | A61F 13/02 |
| | | | 604/304 |
| 2010/0069886 A1 * | 3/2010 | Wilkes | A61M 1/0084 |
| | | | 604/543 |
| 2010/0106106 A1 * | 4/2010 | Heaton | A61M 1/0088 |
| | | | 604/290 |
| 2010/0137775 A1 * | 6/2010 | Hu | A61M 1/0088 |
| | | | 602/54 |
| 2011/0077571 A1 * | 3/2011 | Andresen | A61M 27/00 |
| | | | 602/45 |

(56) References Cited

U.S. PATENT DOCUMENTS

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | H08502194 A | 3/1996 |
| JP | 2001-252349 | 9/2001 |
| JP | 2008-080137 | 4/2008 |
| JP | 2008080137 A | 4/2008 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2008013896 A2 | 1/2008 |
| WO | 2008/036131 A2 | 3/2008 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Ž ivadinovic, V. Ð ukić, Ž . Maksimović, Ð . Radak, and P. Pe š ka, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

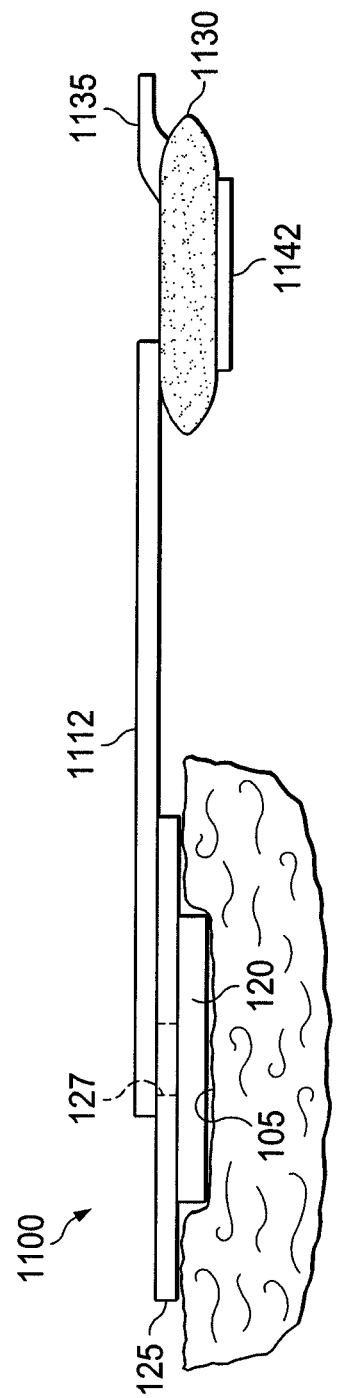

FLUID POUCH, SYSTEM, AND METHOD FOR STORING FLUID FROM A TISSUE SITE

CROSS-REFERENCE TO RELATED APPLICATIONS

This application is a continuation of U.S. patent application Ser. No. 12/617,792, filed Nov. 13, 2009, which claims the benefit of U.S. Provisional Application No. 61/114,827, filed Nov. 14, 2008, each of which is hereby incorporated by reference.

BACKGROUND OF THE INVENTION

1. Field of the Invention

The present application relates generally to medical treatment systems, and more particular, to a fluid pouch, system, and method for storing fluid from a tissue site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

SUMMARY

The problems presented by existing reduced pressure systems are solved by the systems and methods of the illustrative embodiments described herein. In one embodiment, a system for storing fluid removed from a tissue site includes a reduced-pressure source operable to supply reduced pressure and a manifold adapted to distribute the reduced pressure. A drape is provided for covering the manifold, and the drape includes an aperture through which liquid from the tissue site is transferred. A flexible fluid pouch is provided in fluid communication with the aperture and is positioned adjacent the drape. The fluid pouch includes at least one baffle and a fluid channel at least partially defined by the at least one baffle. The fluid channel is operable to store liquid from the tissue site when the reduced pressure is applied through the fluid channel.

In another embodiment, an apparatus for storing liquid from a tissue site includes a drape having an aperture and a fluid pouch in fluid communication with the aperture. The fluid pouch includes at least one baffle and a fluid channel at least partially defined by the at least one baffle. The fluid channel is operable to store liquid from the tissue site when reduced pressure is applied through the fluid channel.

In still another embodiment, an apparatus for storing liquid from a tissue site is provided. The apparatus includes a drape having an aperture and an expandable fluid pouch coupled to the drape such that the fluid pouch is in fluid communication with the aperture. The fluid pouch is operable to transfer reduced pressure to the aperture such that the liquid from the tissue site is drawn into the fluid pouch. The fluid pouch includes a cavity that stores the liquid that is drawn from the tissue site.

In yet another embodiment, a method for storing liquid from a tissue site includes applying a drape and a fluid pouch to the tissue site, the drape having an aperture. The fluid pouch includes at least one baffle and a fluid channel at least partially defined by the at least one baffle. The fluid channel is operable to store liquid from the tissue site. The method further includes supplying a reduced pressure to the fluid pouch and storing the liquid in the fluid channel.

In another embodiment, a method of manufacturing an apparatus for storing liquid from a tissue site includes forming a flexible fluid pouch. The fluid pouch includes at least one baffle and a fluid channel at least partially defined by the at least one baffle. The fluid channel is operable to store liquid from the tissue site.

Other objects, features, and advantages of the illustrative embodiments will become apparent with reference to the drawings and detailed description that follow.

BRIEF DESCRIPTION OF THE DRAWINGS

FIG. 11 illustrates a partial cross-sectional view of a system for storing fluid from a tissue site in accordance with an illustrative embodiment.

DETAILED DESCRIPTION OF THE PREFERRED EMBODIMENT

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
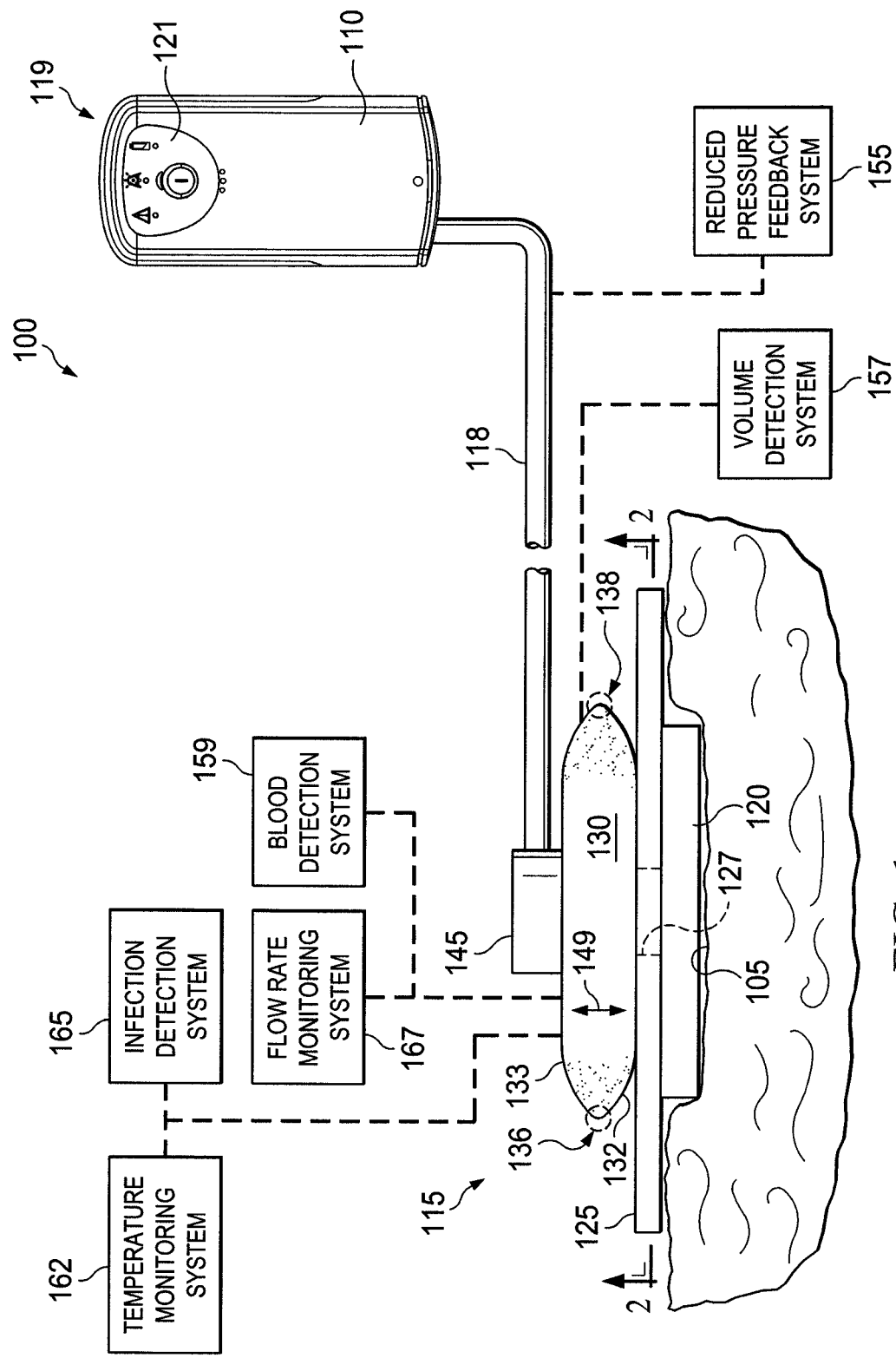
FIG. 1 illustrates a partial cross-sectional view of a system for storing fluid from a tissue site in accordance with an illustrative embodiment.

Referring to FIG. 1, a reduced pressure treatment system 100 for applying a reduced pressure to a tissue site 105 of a patient according to an illustrative embodiment includes a reduced pressure source 110 and a reduced pressure dressing 115 that is positioned at the tissue site 105. In one embodiment, the reduced pressure dressing 115 may include a distribution manifold 120, a cover 125, and a fluid pouch 130, each of which is described in more detail below. The reduced pressure dressing 115 is fluidly connected the reduced pressure source 110 by a conduit 118. The conduit 118 may be any tube through which a gas, liquid, gel, or other fluid may flow. The possible embodiments of the conduit 118 are numerous, and non-limiting examples follow. In addition, the conduit 118 may be made from any material, and may be either flexible or inflexible.

The conduit 118 may include one or more paths or lumens through which fluid may flow. For example, the conduit 118 may include two or more lumens, one of which may be used to deliver reduced pressure to the tissue site and one of which may be used to determine the level of reduced pressure at the tissue site 105. Alternatively, one of the lumens may be used to deliver fluids, such as air, antibacterial agents, antiviral agents, cell-growth promotion agents, irrigation fluids, or other chemically active agents, to the tissue site 105. If fluid delivery is provided by one of the lumens, that particular lumen will likely be configured to bypass the fluid pouch 130.

The conduit 118 may fluidly communicate with the reduced pressure dressing 115 through a tubing adapter 145. The tubing adapter 145 permits the passage of fluid, such as air, from the manifold 120 to the conduit 118, and vice versa. In another embodiment, the reduced-pressure treatment system 100 does not include the tubing adaptor 145. In this embodiment, the conduit 118 may be inserted directly into a component of the dressing 115. The tubing adaptor 145 may be located anywhere relative to the dressing 115. For example, although FIG. 1 shows the tubing adaptor 145 as centrally located relative to the dressing 115, the tubing adaptor 145 may be located at a peripheral portion of the dressing 115.

In the embodiment illustrated in FIG. 1, the reduced pressure source 110 is an electrically-driven vacuum pump. In another implementation, the reduced pressure source 110 may instead be a manually-actuated or manually-charged pump that does not require electrical power. The reduced pressure source 110 instead may be any other type of reduced pressure pump, or alternatively a wall suction port such as those available in hospitals and other medical facilities. The reduced pressure source 110 may be housed within or used in conjunction with a reduced pressure treatment unit 119, which may also contain sensors, processing units, alarm indicators, memory, databases, software, display units, and user interfaces 121 that further facilitate the application of reduced pressure treatment to the tissue site 105. In one example, a sensor or switch (not shown) may be disposed at or near the reduced pressure source 110 to determine a source pressure generated by the reduced pressure source 110. The sensor may communicate with a processing unit that monitors and controls the reduced pressure that is delivered by the reduced pressure source 110.

The reduced-pressure treatment system 100 may include a reduced pressure feedback system 155 operably associated with the other components of the reduced-pressure treatment system 100 to provide information to a user of the reduced-pressure treatment system 100 indicating a relative or absolute amount of pressure that is being delivered to the tissue site 105 or that is being generated by the reduced-pressure source 110. Examples of feedback systems include, without limitation, pop valves that activate when the reduced pressure rises above a selected value and deflection pop valves.

The reduced-pressure treatment system 100 may include a volume detection system 157 to detect the amount of fluid present in the fluid pouch 130, a blood detection system 159 to detect the presence of blood in exudate drawn from the tissue site 105 (including the exudate that is present in the fluid pouch 130), a temperature monitoring system 162 to monitor the temperature of the tissue site 105, an infection detection system 165 to detect the presence of infection at the tissue site 105, and/or a flow rate monitoring system 167 to monitor the flow rate of fluids drawn from tissue site 105. The infection detection system 165 may include a foam or other substance that changes color in the presence of bacteria. The foam or other substance may be operably associated with the dressing 115 or the conduit 118 such that the color changing material is exposed to exudate from the tissue site 105. In addition to the above-mentioned components and systems, the reduced-pressure treatment system 100 may include valves, regulators, switches, and other electrical, mechanical, and fluid components to facilitate administration of reduced-pressure treatment to the tissue site 105.

The distribution manifold 120 is adapted to be positioned at the tissue site 105, and the cover 125, or drape, is positioned over the distribution manifold 120 to maintain reduced pressure beneath the cover 125 at the tissue site 105. The distribution manifold 120 of the reduced pressure dressing 115 is adapted to contact the tissue site 105. The distribution manifold 120 may be partially or fully in contact with the tissue site 105 being treated by the reduced pressure dressing 115. When the tissue site 105 is a wound, the distribution manifold 120 may partially or fully fill the wound.

The distribution manifold 120 may be any size, shape, or thickness depending on a variety of factors, such as the type of treatment being implemented or the nature and size of the tissue site 105. For example, the size and shape of the distribution manifold 120 may be customized by a user to cover a particular portion of the tissue site 105, or to fill or partially fill the tissue site 105. The distribution manifold 120 may have, for example, a square shape, or may be shaped as a circle, oval, polygon, an irregular shape, or any other shape.

In one illustrative embodiment, the distribution manifold 120 is a foam material that distributes reduced pressure to the tissue site 105 when the distribution manifold 120 is in contact with or near the tissue site 105. The foam material may be either hydrophobic or hydrophilic. In one non-limiting example, the distribution manifold 120 is an open-cell, reticulated polyurethane foam such as GranuFoam® dressing available from Kinetic Concepts, Inc. of San Antonio, Tex. If an open-cell foam is used, the porosity may vary, but is preferably about 400 to 600 microns. The flow channels allow fluid communication throughout the portion of the manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through the manifold 120.

In the example in which the distribution manifold 120 is made from a hydrophilic material, the distribution manifold 120 also functions to wick fluid away from the tissue site 105, while continuing to provide reduced pressure to the tissue site 105 as a manifold. The wicking properties of the distribution manifold 120 draw fluid away from the tissue site 105 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The distribution manifold 120 may further promote granulation at the tissue site 105 when a reduced pressure is applied through the reduced pressure dressing 115. For example, any or all of the surfaces of the distribution manifold 120 may have an uneven, coarse, or jagged profile that causes microstrains and stresses at the tissue site 105 when reduced pressure is applied through the distribution manifold 120. These microstrains and stresses have been shown to increase new tissue growth.

In one embodiment, the distribution manifold 120 may be constructed from bioresorbable materials that do not have to be removed from a patient's body following use of the reduced pressure dressing 115. Suitable bioresorbable materials may include, without limitation, a polymeric blend of polylactic acid (PLA) and polyglycolic acid (PGA). The polymeric blend may also include without limitation polycarbonates, polyfumarates, and capralactones. The distribution manifold 120 may further serve as a scaffold for new cell-growth, or a scaffold material may be used in conjunction with the distribution manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Figure 2:
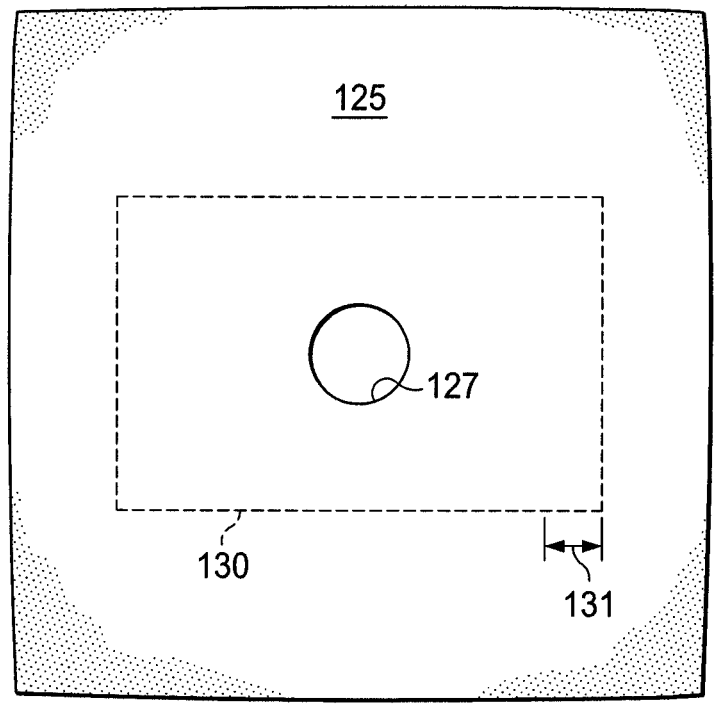
FIG. 2 illustrates a cross-sectional bottom view of a cover and a fluid pouch of the system of FIG. 1 taken along line 2-2.

Referring still to FIG. 1, but also to FIG. 2, the cover 125 covers at least a portion of the manifold 120. As used herein, the term "cover" includes partially or fully covering. Also, a first object that covers a second object may directly or indirectly touch the second object, or may not touch the second object at all. The manifold 120 may be secured to the tissue site 105 using the cover 125. The possible embodiments of the cover 125 are numerous, and non-limiting examples follow. While the cover 125 may be impermeable or semi-permeable, in one example the cover 125 is capable of maintaining a reduced pressure at the tissue site 105 after installation of the cover 125 over the manifold 120. The cover 125 may be a flexible drape or film made from a silicone based compound, acrylic, polyurethane, hydrogel or hydrogel-forming material, or any other biocompatible material that includes the impermeability or permeability characteristics desired for the tissue site 105. The cover 125 may be formed of a hydrophobic material to prevent moisture absorption by the cover 125.

In the embodiment illustrated in FIG. 2, the cover 125 has a square shape. However, the cover 125 may have any shape, such as an elliptical, elongated, irregular, polygonal, or human-customized shape. The cover 125 may be provided in "sheet" form, or in a pourable or sprayable form that is applied over the manifold 120 after placement of the manifold 120 in contact with the tissue site 105. The cover 125 may include a device that is placed over the manifold 120 and the tissue site 105 to provide sealing functionality, including but not limited to, a suction cup, a molded cast, and a bell jar.

In one embodiment, the cover 125 is configured to provide a sealed connection with the tissue surrounding the manifold 120 and the tissue site 105. The sealed connection may be provided by an adhesive layer positioned along a perimeter of the cover 125, or on any portion of the cover 125, to secure the cover 125 to the manifold 120 or the tissue surrounding the tissue site 105. The adhesive may be pre-positioned on the cover 125 or may be sprayed or otherwise applied to the cover 125 immediately prior to installing the cover 125. Prior to the application of the cover 125 to the tissue site 105, the adhesive may also be covered by an adhesive support layer or removable backing The adhesive support layer may provide rigidity to the drape prior to application and may also aid in the actual application of the cover 125 onto the tissue site 105. The adhesive support layer may be peeled off or otherwise removed before applying the cover 125 to the tissue site 105.

In one embodiment, the cover 125 has an aperture 127. Liquid, such as exudate, from the tissue site 105 may pass through the cover 125 via the aperture 127. In some instances, the liquid may also contain solid particles.

Although the aperture 127 is shown to have a circular cross-sectional shape in FIG. 2, the aperture 127 may have any cross-sectional shape, such as an elliptical, elongated slit, irregular, polygonal, or human-customized cross-sectional shape. In addition, the aperture 127 is shown to be substantially centered on the cover 125. However, the aperture 127 may be located anywhere on the cover 125, including the peripheral portions of the cover 125.

The dressing 115 also includes the fluid pouch 130, which may be used to store liquid, such as exudate, from the tissue site 105. The fluid pouch 130 may be coupled to the cover 125 such that the fluid pouch 130 is in fluid communication with the aperture 127. In one embodiment, liquid from the tissue site 105 may pass through the aperture 127 and into the fluid pouch 130 as a result of reduced pressure being applied to the dressing 115. A one-way valve may be located at or near the inlet to the fluid pouch 130 so that fluid in the fluid pouch 130 is restrained from entering the aperture 127. As used herein, the term "coupled" includes coupling via a separate object, and also includes direct coupling. In the case of direct coupling, the two coupled objects touch each other in some way. The term "coupled" also encompasses two or more components that are continuous with one another by virtue of each of the components being formed from the same piece of material. Also, the term "coupled" includes chemical coupling, such as via a chemical bond. The term "coupled" may also include mechanical, thermal, or electrical coupling. The term "coupled" may also include fluidly coupled, in which case a first object that is coupled to a second object is in fluid communication with that second object.

In another embodiment, the fluid pouch 130 may be positioned adjacent or in contact with the cover 125. The term "adjacent" as used herein refers to the positional relationship of two or more objects. Two objects that are adjacent includes two objects that are close to one another and that may, but do not necessarily have to, contact one another. An object that is adjacent to another object may be immediately adjacent with no intervening structure between the two objects, or alternatively, may include two objects that have intervening structures or objects between the two objects.

The fluid pouch 130 may include baffles, which help define fluid channels, for directing fluid flow as will be described further below. Numerous illustrative embodiments of the fluid pouch 130 are possible and a number of illustrative embodiments follow.

In an embodiment, such as that illustrated in FIG. 1, the fluid pouch 130 includes a first sheet 132 and a second sheet 133. In another example, the first sheet 132 and the second sheet 133 may be a first wall and a second wall, respectively. In this embodiment, a perimeter portion of the first sheet 132 may be coupled to a perimeter portion of the second sheet 133. An example of the width of the perimeter portion of either or both of the first sheet 132 and the second sheet 133 is represented by indicator 131 (shown in FIG. 2). However, the perimeter portion 131 may be any size that is able to facilitate the coupling between the first sheet 132 and the second sheet 133. Areas 136 and 138 represent the areas at which the first sheet 132 is coupled to the second sheet 133, as shown in the schematic view of FIG. 1. In one embodiment, non-peripheral portions of the first sheet 132 may also be coupled to non-peripheral portions of the second sheet 133. In another embodiment, at least a portion of each of the first sheet 132 and the second sheet 133 are formed from a single piece of continuous material; in this embodiment, all of the first sheet 132 and the second sheet 133 may be formed from a single piece of continuous material. The first sheet 132 may be coupled to the cover 125.

In one embodiment, either or both of the first sheet 132 and the second sheet 133 is transparent. The transparency of either or both of the first sheet 132 and the second sheet 133 exposes the amount of liquid from the tissue site 105 that is stored in the fluid pouch 130. Thus, a person is made aware of the remaining liquid capacity of the fluid pouch 130 and the possible need to replace or empty the fluid pouch 130.

In another embodiment, the fluid pouch 130 is an expandable fluid pouch that expands as liquid from the tissue site 105 fills the fluid pouch 130. In one non-limiting example, the fluid pouch 130 may expand in either or both of the directions indicated by bi-directional arrow 149 as liquid from the tissue site 105 fills the fluid pouch 130. However, the fluid pouch 130 may expand in other directions as well. The edges of the fluid pouch 130 may also have a pleated construction to facilitate the expansion of the fluid pouch 130.

The fluid pouch 130 may be made from any material, such as a flexible, stretchable, expandable, and/or rigid material. Non-limiting examples of the materials from which the fluid pouch 130 may be made include polymer films of various thicknesses including polyurethane, polypropylene, PVC, polyethylene, and/or polyamides, as well as coated fabrics or laminations of any one or combination of the above.

In one embodiment, a method for storing liquid from the tissue site 105 may include applying the manifold 120 to the tissue site 105 and at least partially covering the manifold 120 with the cover 125. In another embodiment, the cover 125 may be applied directly to the tissue site 105 without the manifold 120. In another embodiment, the method may include applying the cover 125 and a fluid pouch to the tissue site; in this embodiment, either or both of the cover 125 and the fluid pouch may or may not directly touch the tissue site. In another embodiment, the method may also include coupling a fluid pouch as in any of the illustrative embodiment disclosed herein to the cover 125 such that the fluid pouch is in fluid communication with the aperture 127. The method may also include supplying a reduced pressure from the reduced-pressure source 110. The reduced pressure may be supplied to the tissue site 105, the manifold 120, and/or the fluid pouch 130. The reduced pressure may also cause liquid, such as exudate, from the tissue site 105 to enter the fluid pouch 130. The liquid may be stored in the fluid pouch 130.

In another embodiment, a method of manufacturing an apparatus for storing liquid from the tissue site 105 may include forming a fluid pouch as in any of the illustrative embodiments disclosed herein, including the fluid pouch 130. In another embodiment, the method may also include providing the cover 125 and coupling the fluid pouch 130 to the cover 125 such that the fluid pouch 130 is in fluid communication with the aperture 127. In another embodiment, the method may also include providing the manifold 120, and covering at least a portion of the manifold 120 with the cover 125.

Figure 3:
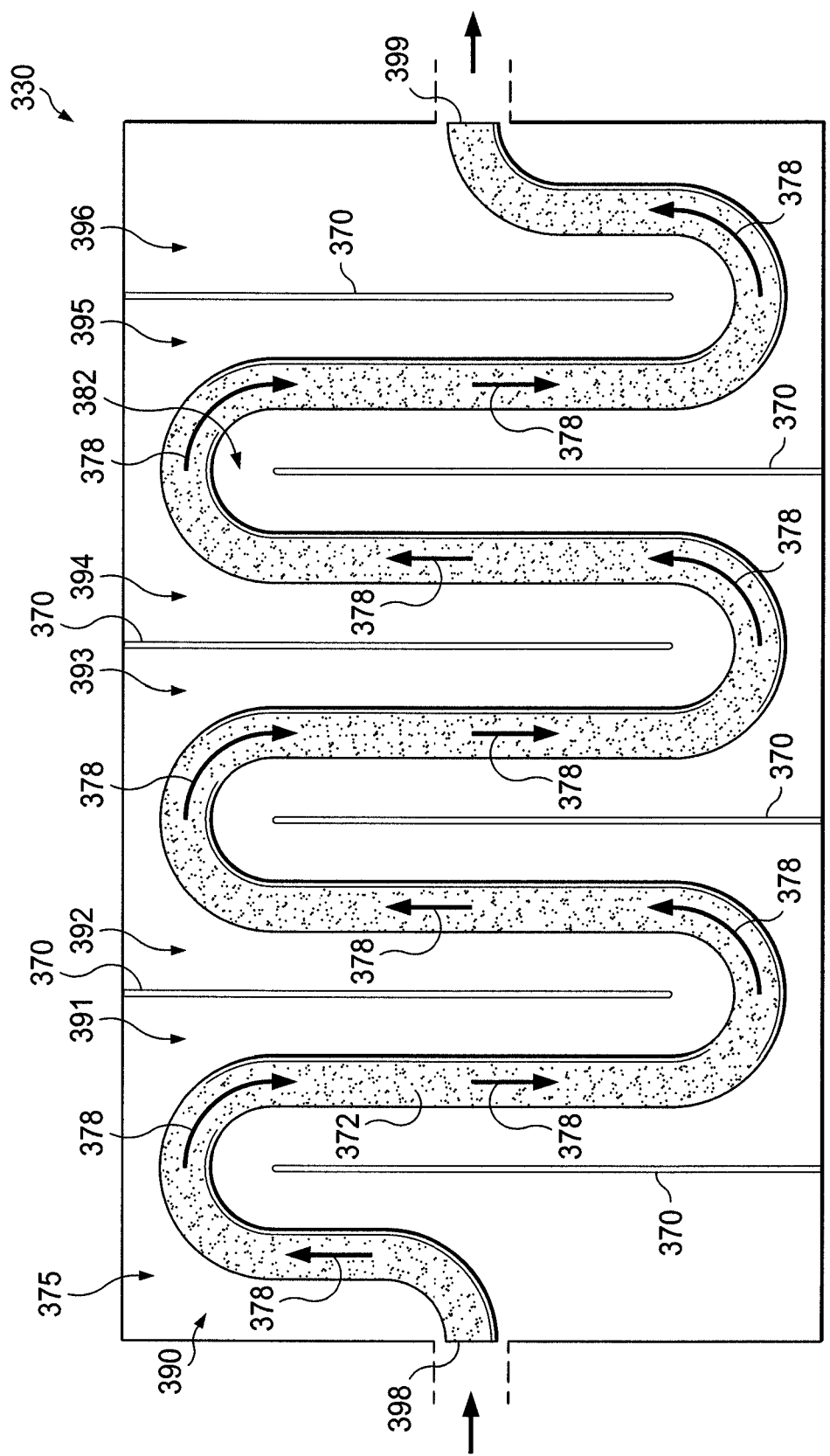
FIG. 3 illustrates a cross-sectional top view of a fluid pouch for storing fluid from a tissue site in accordance with an illustrative embodiment.

Referring to FIG. 3, a fluid pouch 330, which is a non-limiting example of the fluid pouch 130 in FIG. 1, is shown according to an illustrative embodiment. The fluid pouch 330 includes a plurality of baffles 370 that partially defines a fluid channel 375. Reduced pressure from a reduced-pressure source, such as reduced-pressure source 110 in FIG. 1, as well as liquid from the tissue site 105, may move along the fluid channel 375 in a direction indicated by arrows 378. The baffles 370 may direct the flow of liquid through the fluid channel 375. The fluid channel 375 may also store the liquid from the tissue site 105. The baffles 370, as well as the fluid channel 375 formed therefrom, may help prevent liquid from a tissue site from traveling past the fluid pouch 330 and into other components in a reduced-pressure treatment system, such as the tubing adaptor 145 or the delivery tube 135 in FIG. 1.

All of the baffles 370 are substantially parallel to one another to form a plurality of fluid channel portions 390-396 of fluid channel 375. Each of the fluid channel portions 390-396 are in fluid communication with an adjacent fluid channel portion. Such fluid communication is facilitated by gaps 382 between the baffles 370 and a wall of the fluid pouch 330.

The fluid pouch 330 may include any number of baffles and any number of fluid channel portions. For example, the number of baffles and fluid channel portions may be varied to increase or decrease the liquid storage capacity of the fluid pouch 330. The length of the fluid channel 375 or the fluid channel portions 390-396 may also be increased or decreased to vary the liquid storage capacity of the fluid pouch 330.

All of the fluid channel portions 390-396 may be substantially parallel to one another to form a plurality of rows. The fluid pouch 330 includes such a row-like structure. At least two of the fluid channel portions 390-396 are at least partially defined by a same baffle, including any one of baffles 370. For example, both of fluid channel portions 390 and 391 are partially defined by the same baffle because one side of the shared baffle defines a wall of the fluid channel portion 390 and an opposite side of the shared baffle defines a wall of the fluid channel portion 391. Similarly, each of fluid channel portions 393 and 394 are partially defined by the same baffle because one side of the shared baffle defines a wall of the fluid channel portion 393 and an opposite side of the shared baffle defines a wall of the fluid channel portion 394.

For any two fluid channel portions that share a same baffle, a direction of fluid flow in a first of the fluid channel portions may be in an opposite direction than a direction of fluid flow for a second of the fluid channel portions. For example, fluid channel portions 390 and 391, which are partially defined by a same baffle, have fluid flow directions that are opposite from one another, as indicated by arrows 378. Similarly, fluid channel portions 393 and 394, which are partially defined by a same baffle, have fluid flow directions that are opposite from one another, as indicated by arrows 378.

The fluid pouch 330 also includes an inlet 398 and an outlet 399. Liquid from the tissue site 105 enters the fluid channel 375 via the inlet 398. In one embodiment, a reduced-pressure source causes a gas, such as air, to enter the inlet 398, pass through the fluid channel 375, and exit the outlet 399 to cause a reduced pressure to be transferred though the fluid channel 375 and applied to a tissue site. As a result of this reduced pressure, liquid from the tissue site may pass through an aperture in a drape and enter the fluid pouch 330 via the inlet 398. The inlet 398 may also include a one-way valve that allows gas and/or liquid to enter the fluid pouch 330, but does not allow gas and/or liquid to exit the fluid pouch 330 via the inlet 398. In addition, the outlet 399 may include a one-way valve that allows gas to exit the fluid pouch 300, but does not allow gas to enter the fluid pouch 330 via the outlet 399. The outlet 399 may include a liquid-air separator, such as a hydrophobic filter or oleophobic filter, to prevent liquids from exiting the fluid pouch 330.

In one embodiment, the fluid pouch 330 may also include a tube that fluidly couples the aperture (e.g., aperture 127 in FIG. 2) in a drape to the inlet 398. Thus, liquid from the tissue site may pass through the aperture, through the tube, and into the inlet 398. The fluid pouch may also include a tube that fluid couples the outlet 399 to either or both of the tubing adaptor 145 or the conduit 118 in FIG. 1. Providing such tubes may allow the fluid pouch to have any orientation relative to other components in the reduced-pressure treatment system, such as reduced-pressure treatment system 100 in FIG. 1.

The fluid channel 375 may also store liquid from the tissue site, including any liquid that enters the fluid channel 375 via the inlet 398. In one embodiment, the fluid pouch 330 includes an absorbent material 372 in the fluid channel 375. The absorbent material 372 stores, or immobilizes, the liquid from a tissue site.

The absorbent material 372 may be any substance capable of storing a liquid, such as exudate. For example, the absorbent material 372 may form a chemical bond with exudate from the tissue site. Non-limiting examples of the absorbent material 372 include super absorbent fiber/particulates, hydrofibre, sodium carboxymethyl cellulose, and/or alginates. In addition, the fluid channel 375 may include any amount of absorbent material 372. For example, the amount of absorbent material 372 may be varied to increase or decrease the liquid storage capacity of the fluid pouch 330. The presence of the absorbent material 372 may also help to minimize fluid loss or reflux.

Figure 4:
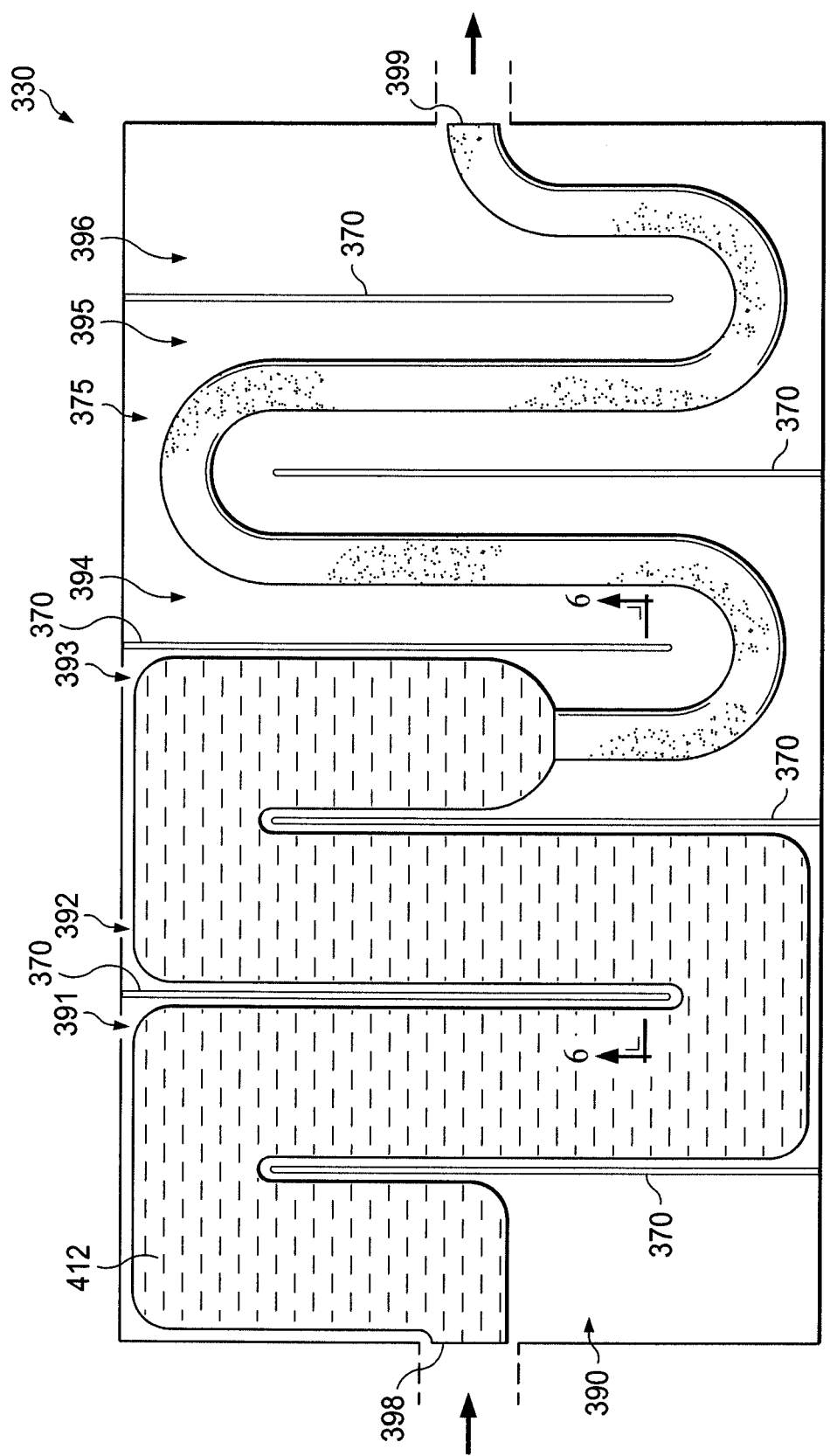
FIG. 4 illustrates a cross-sectional top view of the fluid pouch of FIG. 3 partially filled with liquid from the tissue site.

Referring to FIG. 4, the fluid pouch 330 is shown according to another illustrative embodiment. In particular, FIG. 4 shows the fluid pouch 330 having liquid 412 from a tissue site stored in the fluid channel 375. The fluid channel 375 is partially filled with the liquid 412 from the tissue site.

Reduced pressure that is introduced into the fluid channel 375 via the outlet 399 causes the liquid 412 to enter the fluid channel 375 via the inlet 398. The liquid 412 at least partially occupies fluid channel portions 390-393, while fluid channel portions 394-396 contain little or none of the liquid 412.

In another embodiment, the absorbent material 372 may occlude the fluid channel 375 when all of the absorbent material 372 in the fluid channel 375 is saturated with the liquid 412. Occluding the fluid channel 375 in this manner prevents reduced pressure from being transferred through the fluid pouch 330, and may possibly prevent spillage or overflow of the liquid 412 from the fluid pouch 330.

In another embodiment, the fluid pouch 330 may have multiple fluid channels that may or may not be in fluid communication with one another. In addition, the fluid pouch 330 may have more than one inlet and/or outlet. In the embodiment in which the fluid pouch 330 has more than one fluid channel, each of the fluid channels may have a respective inlet and/or outlet.

Figure 5:
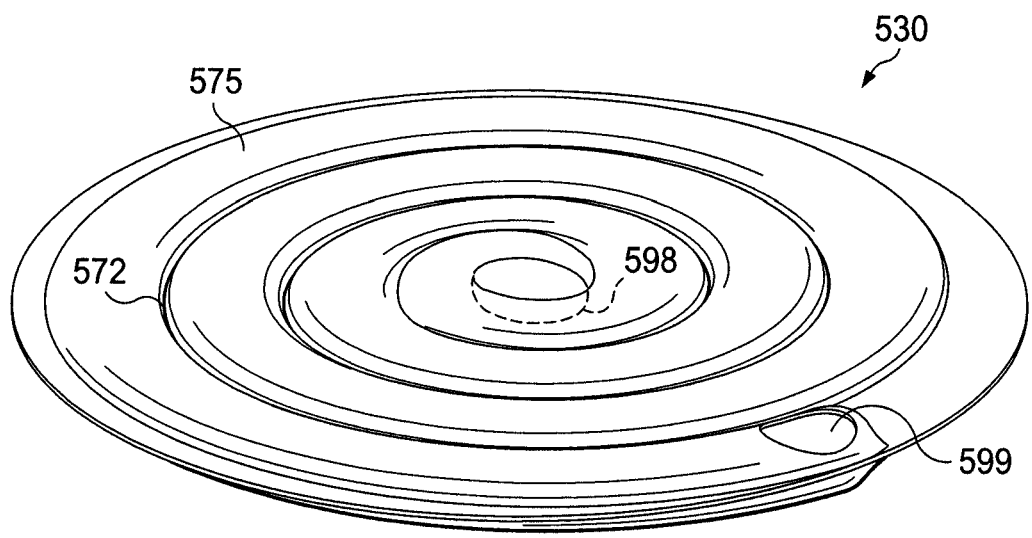
FIG. 5 illustrates a perspective view of a fluid pouch for storing fluid from a tissue site in accordance with an illustrative embodiment.

Referring to FIG. 5, a fluid pouch 530 is shown according to an illustrative embodiment. In contrast to the fluid pouch 330 in FIGS. 3 and 4, the fluid pouch 530 has a circular shape. In other embodiments, the fluid pouch may also have any other shape, such as an elliptical, polygonal, irregular, or user-customized shape.

A baffle 572 of fluid pouch 530 is a spiraling baffle that emanates from a central portion of the fluid pouch 530. In addition, a fluid channel 575 emanates from a central inlet 598 to form a spiraling fluid channel that is at least partially defined by the spiraling baffle 572. The central inlet 598 is functionally analogous to the inlet 398 in FIGS. 3 and 4. The central inlet 598 may be adjacent, abutting, or otherwise in fluid communication with an aperture in a drape, such as the aperture 127 in the cover 125 in FIG. 1, such that liquid from a tissue site passes through the aperture and enters the fluid channel 575 of the fluid pouch 530 via the central inlet 598. A coupling member might also be used in coupling the inlet 598 and the aperture.

Although no absorbent material, such as absorbent material 372, is shown in the fluid pouch 530, the fluid channel 575 may include an absorbent material as described in any of the illustrative embodiments herein. Also, the number of revolutions of the fluid channel 575 around the central inlet 598 may be varied to increase or decrease the liquid storage capacity of the fluid pouch 530.

Outlet 599 is functionally analogous to the outlet 399 in FIGS. 3 and 4. The outlet 599 may be located at an end of the fluid channel 575 in a periphery portion of the fluid pouch 530. In one embodiment, a reduced-pressure source causes a gas, such as air, to enter the central inlet 598, pass through the fluid channel 575, and exit the outlet 599 to cause a reduced pressure to be transferred though the fluid channel 575 and applied to a tissue site. As a result of this reduced pressure, liquid from the tissue site may pass through an aperture in a drape and enter the fluid pouch 530 via the central inlet 598. In one embodiment, the position of the central inlet 598 and the outlet 599 may be reversed such that the outlet 599 is at a central portion of the fluid pouch 530 and the central inlet 598 is at a peripheral portion of the fluid pouch 530.

Figure 6:
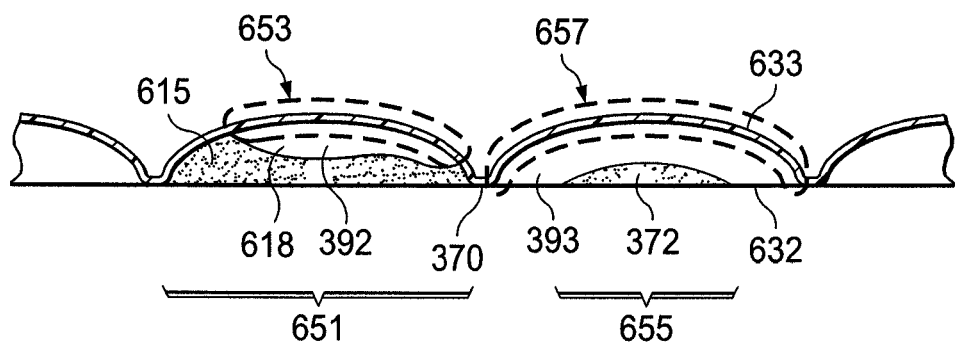
FIG. 6 illustrates a cross-sectional side view of a portion of the fluid pouch of FIG. 4 taken at 6-6.

Referring to FIG. 6, a cross-sectional view of the fluid pouch 330 taken along line 6-6 in FIG. 4 is shown. In particular, FIG. 6 shows fluid channel portions 392 and 393, each of which includes absorbent material 372. The fluid channel portion 392 includes a covered portion 651 that is covered by a saturated absorbent material 615. The saturated absorbent material 615 is the absorbent material 372, such as that shown in FIGS. 3 and 4, which is saturated with liquid, such as exudate, from a tissue site. The fluid channel portion 392 also includes an uncovered portion 653 that is uncovered by an absorbent material. The fluid channel portion 393 includes a covered portion 655 that is covered by the absorbent material 372 and an uncovered portion 657 that is uncovered by the absorbent material 372. The thickness of the absorbent material 372 on the covered portions 651 and 655 may be varied to increase or decrease the storage capacity of the fluid pouch.

The fluid channel portions 392 and 393 are formed by coupling portions of sheet 633 to sheet 632. The sheet 632 is substantially flat and the sheet 633 includes curved portions over the fluid channel portions 392 and 393. In one embodiment, the absorbent material 372 covers at least a portion of the sheet 632. The sheet 633 may be uncovered by the absorbent material 372. In addition, an inner portion of the sheet 633 is adhered to an inner portion of the sheet 632 to form the baffle 370. An inner portion of the sheet 633 may be adhered to an inner portion of the sheet 632 in a variety of ways. For example, an inner portion of the sheet 633 may be welded, glued, sewed, pinned, snapped, or otherwise bonded onto an inner portion of the sheet 632. In the example in which an inner portion of the sheet 633 is welded onto an inner portion of the sheet 632, the welding may be achieved using heat, ultrasonics, radio frequencies, a solvent, and/or other welding methods.

In one embodiment, the fluid channel portion 392 includes a passageway 618 through which reduced pressure is transferable when the absorbent material 615 is saturated with liquid from the tissue site. In this embodiment, the passageway 618 is present in the fluid channel portion 392 when the absorbent material 615 is partially or fully saturated with liquid. By maintaining the passageway 618 when the absorbent material 615 is saturated with liquid, reduced pressure from a reduced-pressure source may continue to be transferred to a tissue site via the fluid pouch.

Figure 7:
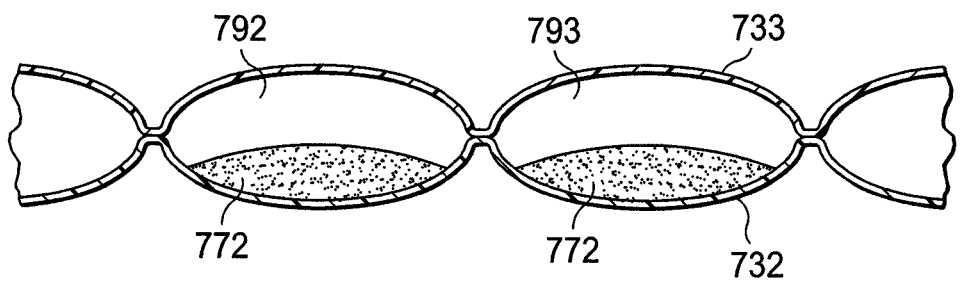
FIG. 7 illustrates a cross-sectional side view of a portion of a fluid pouch for storing fluid from a tissue site in accordance with an illustrative embodiment.

Referring to FIG. 7, a cross-sectional view of fluid channel portions 792 and 793 of a fluid pouch is shown according to an illustrative embodiment. The fluid channel portions 792 and 793 include absorbent material 772, which covers a portion of the sheet 732. In contrast to the sheet 632 in FIG. 6, the sheet 732 is curved at the fluid channel portions 792 and 793. Thus, the walls of each of the fluid channel portions 792 and 793 formed by each of the sheets 732 and 733 are curved.

Figure 8:
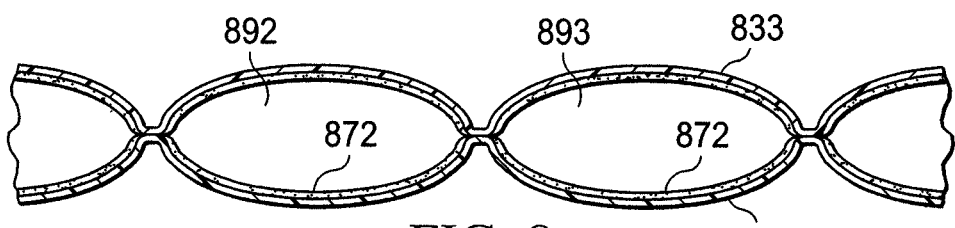
FIG. 8 illustrates a cross-sectional side view of a portion of a fluid pouch for storing fluid from a tissue site in accordance with an illustrative embodiment.

Referring to FIG. 8, a cross-sectional view of fluid channel portions 892 and 893 of a fluid pouch is shown according to an illustrative embodiment. In FIG. 8, the inner surfaces of both sheets 832 and 833 are covered with the absorbent material 872. In this embodiment, an entire inner surface of the fluid channel may be covered with the absorbent material 872. The thickness of the absorbent material 872 on the inner surface of the fluid channel may be varied to increase or decrease the storage capacity of the fluid pouch.

Figure 9:
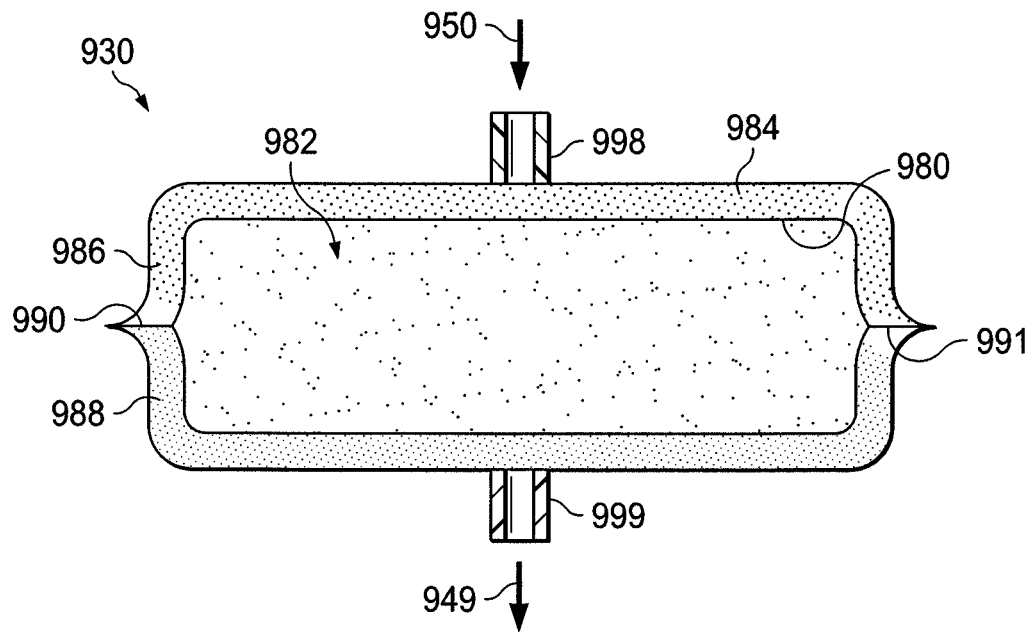
FIG. 9 illustrates a cross-sectional side view of a fluid pouch for storing fluid from a tissue site in accordance with an illustrative embodiment.

Referring to FIG. 9, a fluid pouch 930 is shown according to an illustrative embodiment. The fluid pouch 930 does not contain baffles. The fluid pouch 930 is operable to transfer reduced pressure to an aperture, such as aperture 127 in FIG. 1, such that the liquid from a tissue site is drawn into the fluid pouch 930. The aperture would be proximate inlet 998. A gas, such as air, may be drawn from the fluid pouch 930 via outlet 999 such that reduced pressure is transferred to a tissue site via the aperture. The movement of gas that may be drawn by a reduced-pressure source is represented by arrow 949. The fluid pouch 930 has a cavity 980 that stores the liquid that is drawn from the tissue site.

In one embodiment, no absorbent material is contained in the cavity 980. In another embodiment, the cavity 980 includes absorbent material 982. The absorbent material 982 is analogous to the absorbent material 372 in FIG. 3, and may be composed of a same or similar material. As the liquid from a tissue site passes through the inlet 998 and enters the cavity 980, the absorbent material 982 may absorb and store the liquid. The movement of liquid from the tissue site into the inlet 998 is represented by arrow 950. The fluid pouch 930, and particularly cavity 980, may expand as liquid fills the cavity 980.

The fluid pouch 930 may be formed with an envelope 984 that at least partially encloses the cavity 980. In one embodiment, the envelope 984 fully encloses the cavity 980. The envelope 984 may be composed of any of a variety of materials. In one embodiment, the envelope 984 may be composed of a same or similar material as fluid pouch 130 in FIG. 1.

In one embodiment, the envelope 984 may be a manifolding envelope that may be composed of a material that is operable to distribute and/or transfer a liquid, including exudate from a tissue site. For example, the envelope 984 may be composed of an open-cell foam. In this example, the open-cell foam may be reticulated or non-reticulated, and may be hydrophobic or hydrophilic. In another example, the envelope 984 may be made from a non-woven material, including a non-woven material manufactured by Libeltex, Dupont, Freudenberg, or Ahlstrom. In another example, the envelope 984 may be composed of a three dimensional material, including Supracor® fusion bonded honeycomb or XD spacer fabric manufactured by Baltex. In another example, the envelope 984 may be composed of a molded matrix.

The envelope 984 may be composed of layers 986 and 988. In the embodiment in which the envelope 984 is a manifolding envelope, the layers 986 and 988 may be manifolding layers. A perimeter of the layer 986 may be bonded to a perimeter of the layer 988 at bonding sites 990 and 991. Any bonding method may be used, including those previously mentioned for welding.

Figure 10:
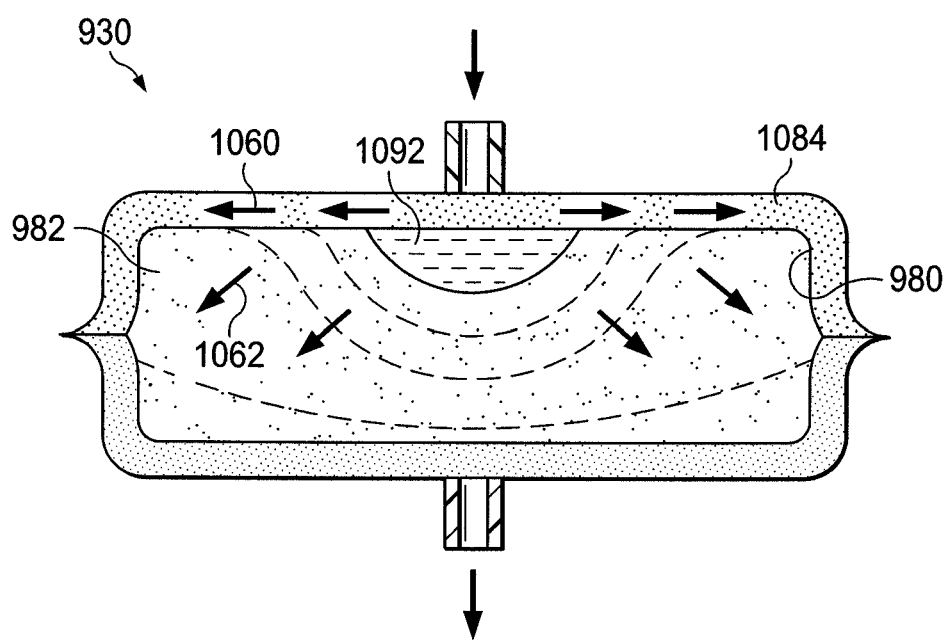
FIG. 10 illustrates a cross-sectional view of a fluid pouch for storing fluid from a tissue site in accordance with an illustrative embodiment.

Turning now to FIG. 10, a fluid pouch 930 is shown according to an illustrative embodiment. The fluid pouch 930 includes a manifolding envelope 1084 that distributes liquid 1092 from a tissue site along at least a portion of the perimeter of the cavity 980. The absorbent material 982 absorbs the liquid 1092, which is stored in the cavity 980. The movement of the liquid 1092 through the absorbent material 982 in the cavity 980 is represented by arrows 1062.

In addition, the manifolding envelope 1084 distributes liquid 1092 along a perimeter of the cavity 980 in a direction indicated by arrows 1060. Without the manifolding envelope 1084, in some circumstances the absorbent material 982 may swell in the immediate area of liquid entry into the cavity 980, and possibly cause a restriction in flow before much of the absorbent material 982 is used. The manifolding envelope 1084 helps to ensure that a greater portion of the absorbent material 982 is exposed to the liquid 1092, thereby facilitating larger and more efficient liquid storage.

Referring to FIG. 11, a reduced-pressure treatment system 1100 is shown according to an illustrative embodiment. Manifold 120 has been applied to the tissue site 105, and the cover 125 covers the manifold 120. The reduced-pressure treatment system 1100 also includes fluid pouch 1130.

The reduced-pressure treatment system 1100 includes a connection tube 1112. The cover 125 is coupled to the fluid pouch 1130 via the connection tube 1112 such that the connection tube 1112 facilitates fluid communication between the aperture 127 and the fluid pouch 1130. One end of the connection tube 1112 is fluidly coupled to the aperture 127, and another end of the connection tube 1112 is fluidly coupled to an inlet of a fluid pouch 1130. In one embodiment, the connection tube 1112 allows the fluid pouch 1130 to be remotely located from the manifold 120 and/or the cover 125. Fluid may exit the fluid pouch 1130 via an outlet connector 1135, which is functionally analogous to the tubing adaptor 145 in FIG. 1.

In one example, the fluid pouch 1130 may be located on a patient's skin at a site that is adjacent or remote from the manifold 120 and/or the cover 125. In this example, the fluid pouch 1130 may be adhered to the patient's skin and/or clothing using adhesive layer 1142 and/or a mechanical connection (e.g., strap). In another example, the fluid pouch 1120 may be connected to or mated with any object that is remote from the manifold 120 and/or the cover 125. For example, the fluid pouch may mate with a hospital bed, wheel chair, and/or walking boot. The fluid pouch 1130 may be adhered to an object or person using any means of adherence.

It should be apparent from the foregoing that an invention having significant advantages has been provided. While the invention is shown in only a few of its forms, it is not just limited but is susceptible to various changes and modifications without departing from the spirit thereof.

We claim:

1. A system for storing fluid from a tissue site, the system comprising:
    a manifold adapted to be positioned over the tissue site to distribute reduced pressure;
    a drape adapted to cover the manifold and skin adjacent to the tissue site to form a sealed space, the drape having an aperture; and
    a pouch adapted to be positioned adjacent to the drape and fluidly coupled to the aperture, the pouch having at least one baffle forming a first fluid channel portion and a second fluid channel portion so that a direction of fluid flow in the first channel portion is in a substantially opposite direction from a direction of fluid flow in the second channel portion, at least one of the first fluid channel portion and the second fluid channel portion adapted to contain liquid from the tissue site.

2. The system of claim 1, wherein the pouch further comprises an absorbent material disposed in the first fluid channel portion and the second fluid channel portion.

3. The system of claim 2, wherein the absorbent material covers at least a portion of the first fluid channel portion and the second fluid channel portion.

4. The system of claim 2, wherein the first fluid channel portion and the second fluid channel portion include a passageway through which reduced pressure is transferable if the absorbent material is saturated with liquid from the tissue site.

5. The system of claim 1, wherein the pouch comprises:
    a first sheet having a perimeter portion;
    a second sheet having a perimeter portion; and
    wherein the perimeter portion of the first sheet is coupled to the perimeter portion of the second sheet.

6. The system of claim 5, wherein the first sheet is coupled to the drape.

7. The system of claim 5, wherein the at least one baffle comprises at least one inner portion of the first sheet adhered to at least one inner portion of the second sheet.

8. The system of claim 1, wherein the baffle forms a wall of the first fluid channel portion and the second fluid channel portion, the wall having a gap to permit fluid communication between the first fluid channel portion and the second fluid channel portion.

9. The system of claim 1, wherein:
    the at least one baffle is a plurality of baffles; and
    the first fluid channel portion and the second fluid channel portion are a plurality of fluid channel portions.

10. The system of claim 1, further comprising a connection tube fluidly coupling the pouch to the aperture of the drape.

11. The system of claim 1, wherein the at least one baffle is a spiraling baffle, and the first fluid channel portion and the second fluid channel portion form a spiraling fluid channel.

12. The system of claim 1, further comprising a reduced-pressure source adapted to be fluidly coupled to the pouch to supply reduced pressure through the pouch to the manifold.

* * * * *